United States Patent [19]

Hrib et al.

[11] Patent Number: 5,240,927

[45] Date of Patent: Aug. 31, 1993

[54] BENZO[β]THIOPHEN-3-YL PIPERAZINES AS ANTIPSYCHOTIC AGENTS

[75] Inventors: Nicholas J. Hrib, Somerville; John G. Jurcak, Union City, both of N.J.

[73] Assignee: Hoechst-Roussel Pharmaceuficals Incorporated, Somerville, N.J.

[21] Appl. No.: 885,331

[22] Filed: May 19, 1992

[51] Int. Cl.$^5$ .................. A61K 31/495; C07D 405/04
[52] U.S. Cl. .................................. 514/254; 544/376; 549/49; 549/57
[58] Field of Search .................. 544/376; 514/254

[56] References Cited

U.S. PATENT DOCUMENTS

| | | | |
|---|---|---|---|
| 4,366,162 | 12/1982 | Björk et al. | 514/327 |
| 4,710,500 | 12/1987 | Perregaard | 514/254 |
| 4,803,203 | 2/1989 | Caprathe et al. | 544/360 |
| 4,879,288 | 11/1989 | Warawa et al. | 514/211 |
| 5,084,454 | 1/1992 | Varasi et al. | 544/70 |

FOREIGN PATENT DOCUMENTS 34521 8/1981 European Pat. Off. ............ 544/376

OTHER PUBLICATIONS

Beck, J. Org. Chem., vol. 37, No. 21, 3224-3226 (1972).
Beck and Yahnder, J. Org. Chem., vol. 39, No. 23, 3440-3441 (1974).
Reinhoudt and Kouwenhoven, Tetrahedron, vol. 30, 2432-2436 (1974).
Geneste, et al, Tetrahedron Letters, No. 28, 2345-2348 (1975).
Geneste, et al. Bull. Soc. Chim. France, 1977, 271-275.

*Primary Examiner*—Emily Bernhardt
*Attorney, Agent, or Firm*—Tatsuya Ikeda

[57] ABSTRACT

There are disclosed various compounds of the formula depicted below,

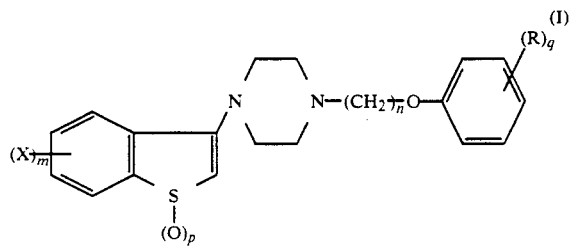

where the parameters m, n, p, q, X and R are as defined in the specification, as being useful as antipsychotic agents.

16 Claims, No Drawings

BENZO[β]THIOPHEN-3-YL PIPERAZINES AS ANTIPSYCHOTIC AGENTS

The present invention relates to compounds having Formula I depicted below,

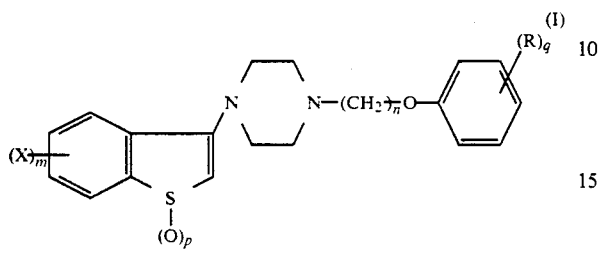

where,
m is an integer of 1 or 2;
each X is independently hydrogen, halogen, loweralkoxy or trifluoromethyl;
n is an integer of 2 or 3;
p is an integer of 0, 1 or 2;
q is an integer of 1 or 2; and
each R is independently hydrogen, loweralkyl, loweralkoxy, hydroxy, —NH-Alkyl,

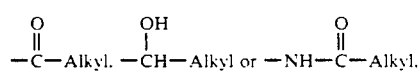

the term "Alkyl" in each occurrence signifying an aklyl group of 1 to 6 carbon atoms;
which compounds are useful as antipsychotic agents.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, isopropyl, iso-butyl, sec-butyl and straight- and branched-chain pentyl and hexyl.

The term halogen shall mean fluorine, chlorine, bromine or iodine.

Throughout the specification and the appended claims, a given chemical formula or name shall encompass all geometric, stereo, optical and tautomeric isomers where such isomers exist.

The compounds of this invention can be prepared by utilizing the following reaction scheme.

Throughout the description of the synthetic steps, the notations m, n, p, q, X and R shall have the respective meanings given above unless otherwise stated or indicated.

STEP A

A 3-amino-2-methoxycarbonyl-benzo[b]thiophene compound of Formula II is allowed to undergo a decarboxylation reaction to afford a compound of Formula III. This reaction can be accomplished in a manner substantially similar to the one used by Perregard, U.S. Pat. No. 4,710,500 for the decarboxylation of 3-hydroxy-2-methoxycarbonylindole.

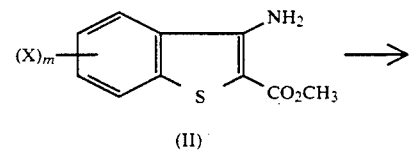

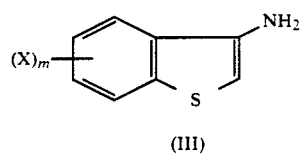

STEP B

Compound III is allowed to react with piperazine in the presence or absence of an acid catalyst to afford a compound of Formula IV. For details of this reaction, the reader is again referred to Perregard, U.S. Pat. No. 4,710,500. One can conduct Steps A and B consecutively without isolating and purifying the intermediate compound of Formula III.

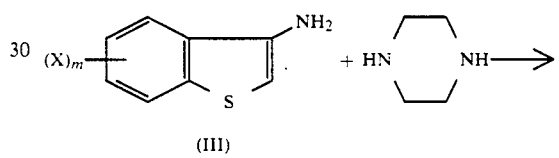

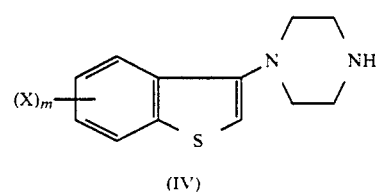

STEP C

A compound of Formula V is oxidized to afford a compound of Formula VI. For details of this reaction, the reader is referred, for instance, to Geneste et al, Bull. Soc. Chim. France, 271 (1977) and Geneste et al, Tetrahedron Letters, 28, 2345 (1975).

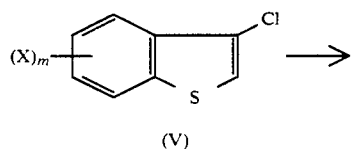

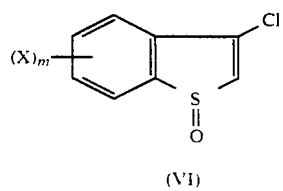

STEP D

Compound VI is allowed to react with piperazine in substantially the same manner as in Step B to afford a compound of Formula VII.

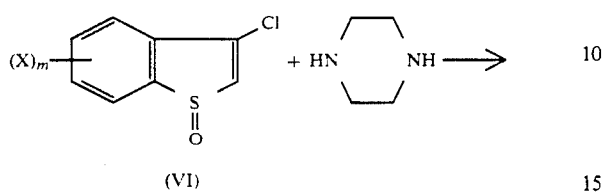

(VI)

(VII)

STEP E

Compound V is oxidized to afford a dioxide compound of Formula VIII. For details of this reaction, the reader is referred, for instance, to Bordwell et al, J. Amer. Chem. Soc. 70, 1558 (1948) and Geneste et al, Bull. Soc. Chim. France, 271 (1977) and Geneste et al, Tetrahedron Letters, 28, 2345.

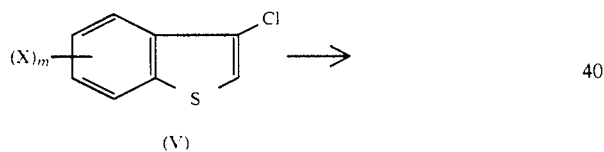

(V)

(VIII)

STEP F

Compound VIII is allowed to react with piperzine in substantially the same manner as in Step D to afford a compound of Formula IX.

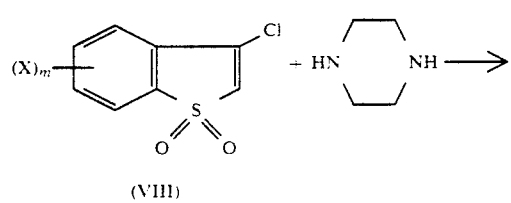

(VIII)

-continued

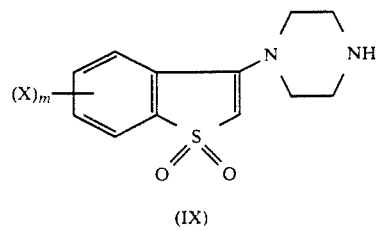

(IX)

STEP G

A compound of Formula X where p is 0, 1 or 2, which is obtained from Step B, D or F, is allowed to react with a chloro or bromo compound of Formula XI where "Hal" is Cl or Br in a routine manner known to the art to afford a target compound of Formula I.

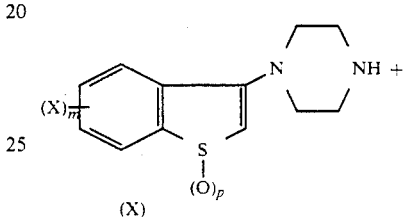

(X)

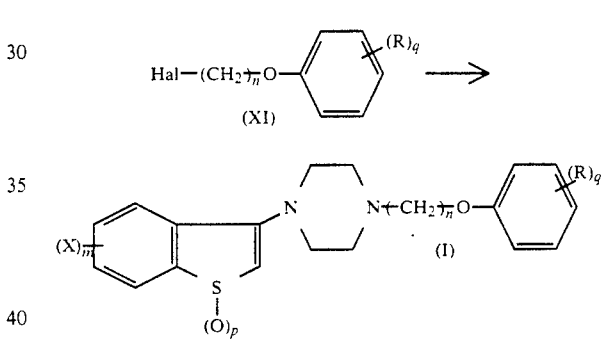

(XI)

(I)

The compounds of Formula I of the present invention are useful for treating psychoses by virtue of their ability to block apomorphine-induced climbing in mammals.

Antipsychotic activity is determined in the climbing mice assay by methods similar to those described by P. Protais et al, Psychopharmacol., 50, 1 (1976) and B. Costal, Eur. J. Pharmacol., 50, 39 (1978).

The subject CK-1 male mice (23-27 grams) are group-housed under standard laboratory conditions. The mice are individually placed in wire mesh stick cages (4"×4" 10) and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, three readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |

| Climbing Behavior | Score |
|---|---|
| 4 paws on the wall (full climb) | 2 |

Mice consistently climbing before the injection of apormorphine are discarded.

With full-developed apomorphine climbing, the animals are hanging onto the cage walls, rather motionless, over longer periods of time. By contrast, climbs due to mere motor stimulation usually last only a few seconds.

The climbing scores are individually totaled (maximal score; 6 per mouse over three readings) and the total score of the control group (vehicle intraperitioneally-apomorphine subcutaneously) is set to 100%. $ED_{50}$ values with 95% confidence limits are calculated by a Linear Regression Analysis. Antipsychotic activity expressed as $ED_{50}$ is presented in Table 1 for a representative compound of this invention as well as for two reference compounds.

TABLE 1

| Antipsychotic Activity (Climbing Mice Assay) | |
|---|---|
| Compound | $ED_{50}$(mg/kg) |
| 1-[4-[3-[4-(6-Fluorobenzo[b]thiophen-3-yl-1-piperazinyl]propoxy]-3-methoxyphenyl]ethanone | 1.42 |
| (Reference Compounds) | |
| Haloperidol | 0.33 |
| Sulpiride | 14.5 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include;
1-[4-[3-[4-(6-Fluorobenzo[b]thiophen-3-yl)-1-piperazinyl]propoxy]-3-methoxyphenyl]ethanone;
1-[4-[3-[4-(6-Chlorobenzo[b]thiophen-3-yl)-1-piperazinyl]propoxy]-3-methoxyphenyl]ethanone S,S-dioxide;
1-[4-[3-[4-(Benzo[b]thiophen-3-yl)-1-piperazinyl]propoxy]-3-methoxyphenyl]ethanone;
N-[3-[3-[4-(6-Fluorobenzo[b]thiophen-3-yl)-1-piperazinyl]propoxy]-4-methoxyphenyl]acetamide;
1-[4-[3-[4-(6-Chlorobenzo[b]thiophen-3-yl)-1-piperazinyl]propoxy]-3-methoxyphenyl]ethanone;
1-[4-[3-[4-(6-Fluorobenzo[b]thiophen-3-yl)-1-piperazinyl]propoxy]-3-(methylamino) phenyl]ethanone;
N-[3-[2-[4-(6-Fluorobenzo[b]thiophen-3-yl)-1-piperazinyl)ethoxy]phenyl]acetamide;
N-[3-[3-[4-Benzo[b]thiophen-3-yl)-1-piperazinyl]propoxy]phenyl]acetamide;
6-Fluoro-3-[4-(3-phenoxypropyl)-1-piperazinyl]benzo[b]thiophene;
1-[4-[3-[4-(6-Fluorobenzo[b]thiophen-3-yl)-1-piperazinyl]propoxy]-3-hydroxyphenyl]ethanone;
4-[3-[4-(6-Fluorobenzo[b]thiophen-3-yl)-1-piperazinyl]propoxy]-3-methoxy-α-methylbenzenemethanol;

6-Fluoro-3-[4-[3-(2-methoxyphenoxy)propyl]-1-piperazinyl]benzo[b]thiophene; and

1-[4-[3-[4-Benzo[b]thiophen-3-yl)-1-piperazinyl]propoxy]-3-methoxyphenyl]ethanone S-oxide.

The following example is presented in order to illustrate the present invention.

EXAMPLE 1

1-[4-[3-[4-(6-Fluorobenzo[b]thiophen-3-yl)-1-piperazinyl]propoxy]-3-methoxyphenyl]ethanone A mixture of 1-[4-(3-bromopropoxy)-3-methoxyphenyl]ethanone (4.42 g), 3-(1-piperazinyl)-6-fluorobenzo[b]thiophene (4.00 g), potassium carbonate (6.40 g), sodium iodide (0.30 g), and dimethylformamide (50 mL) was heated at 65° C. under a nitrogen atmosphere for six hours. The mixture was diluted with 10% sodium hydroxide (300 ml) and extracted with 50% ether/toluene (3 × 100 mL). The combined extracts were washed with water (100 ml) and brine (100 mL), dried (sodium sulfate), and concentrated under reduced pressure. The residue was chromatographed on silica gel (elution with 5% methanol in dichloromethane) to give 3.98 g of gum.

To a solution of the amine (3.62 g), ethanol, and toluene was added a solution of fumaric acid (0.960 g) and ethanol. Concentration of the resulting solution gave a solid which was recrystallized from methanol/ethanol to yield 3.06 g of crystalling material, m.p. 172°-174° C.

Analysis: Calculated for $C_{28}H_{31}FN_2O_7S$: 60.20%C; 5.59%H; 5.01%N. Found: 60.27%C; 5.72%H; 5.05%N.

We claim:

1. A compound of the formula,

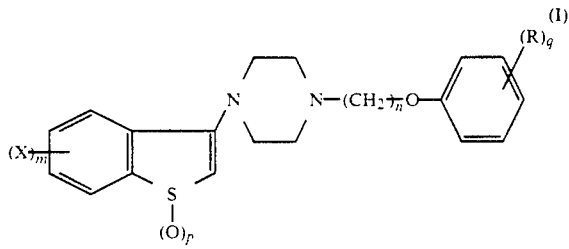

where, m is an integer of 1 or 2;

each X is independently hydrogen, halogen, loweralkoxy or trifluoromethyl;

n is an integer of 2 or 3;

p is an integer of 0, 1 or 2;

q is an integer of 1 or 2; and each R is independently hydrogen, loweralkyl, loweralkoxy, hydroxy, —NH-Alkyl,

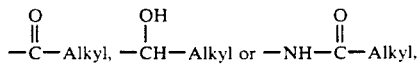

the term "Alkyl" in each occurrence signifying an alkyl group of 1 to 6 carbon atoms;

or a pharmaceutically acceptable acid addition salt thereof.

2. The compound as defined in claim 1, which is 1-[4-[3-[4-(6-fluorobenzo[b]thiophen-3-yl)-1-piperazinyl]propoxy]-3-methoxyphenyl]ethanone.

3. The compound as defined in claim 1, which is 1-[4-[3-[4-(6-chlorobenzo[b]thiophen-3-yl)-1-piperazinyl]propoxy]-3-methoxyphenyl]ethanone S,S-dioxide.

4. The compound as defined in claim 1, which is 1-[4-[3-[4-(benzo[b]thiophenen-3-yl)-1-piperazinyl]propoxy]-3-methoxyphenyl]ethanone.

5. The compound as defined in claim 1, which is N-[3-[3-[4-(6-fluorobenzo[b]thiophen-3-yl)-1-piperazinyl]propoxy]-4-methoxyphenyl]acetamide.

6. The compound as defined in claim 1, which is 1-[4-[3-[4-(6-chlorobenzo[b]thiophen-3-yl)-1-piperazinyl]propoxy]-3-methoxyphenyl]ethanone.

7. The compound as defined in claim 1, which is 1-[4-[3-[4-(6-fluorobenzo[b]thiophen-3-yl)-1-piperazinyl]propoxy]-3-(methylamino) phenyl]ethanone.

8. The compound as defined in claim 1, which is N-[3-[2-[4-(6-fluorobenzo[b]thiophen-3-yl)-1-piperazinyl)ethoxy]phenyl]acetamide.

9. The compound as defined in claim 1, which is N-[3-[3-[4-benzo[b]thiophen-3-yl)-1-piperazinyl]propoxy]phenyl]acetamide.

10. The compound as defined in claim 1, which is 6-fluoro-3-[4-(3-phenoxypropyl)-1-piperazinyl]benzo[b]thiophene.

11. The compound as defined in claim 1, which is 1-[4-[3-[4-(6-fluorobenzo[b]thiophen-3-yl)-1-piperazinyl)propoxy]-3-hydroxyphenyl]ethanone.

12. The compound as defined in claim 1, which is 4-[3-[4-(6-fluorobenzo[b]thiophen-3-yl)-1-piperazinyl]-propoxy]-3-methoxy-α-methylbenzenemethanol.

13. The compound as defined in claim 1, which is 6-fluoro-3-[4-[3-(2-methoxyphenoxy)propyl]-1-piperazinyl]benzo[b]thiophene.

14. The compound as defined in claim 1, which is 1-[4-[3-[4-benzo[b]thiophen-3-yl)-1-piperazinyl]propoxy]-3-methoxyphenyl]ethanone S-oxide.

15. An antipsychotic composition comprising an effective psychosis-alleviating amount of a compound as defined in claim 1.

16. A method of treating a patient in need of relief from psychosis which comprises administering to the patient an effective psychosis alleviating amount of a compound as defined in claim 1.

* * * * *